United States Patent
Clerc et al.

(10) Patent No.: US 8,143,245 B2
(45) Date of Patent: Mar. 27, 2012

(54) USE OF 10-[(3R)-1-AZABICYCLO[2.2.2]OCT-3-YLMETHYL]-10H-PHENOTHIAZINE FOR THE PREPARATION OF A DRUG HAVING A SELECTIVE INHIBITION OF MUSCARINIC $M_1$, $M_2$, AND $M_3$ RECEPTORS

(75) Inventors: Thierry Clerc, Vigoulet Auzil (FR); Jacky Tisne-Versailles, Castres (FR); Christophe Przybylski, Villefranche de Lauragais (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 238 days.

(21) Appl. No.: 12/521,067

(22) PCT Filed: Dec. 26, 2007

(86) PCT No.: PCT/EP2007/064553
§ 371 (c)(1),
(2), (4) Date: Jun. 24, 2009

(87) PCT Pub. No.: WO2008/080924
PCT Pub. Date: Jul. 10, 2008

(65) Prior Publication Data
US 2010/0063276 A1 Mar. 11, 2010

(30) Foreign Application Priority Data
Dec. 28, 2006 (FR) .................................... 06 56002

(51) Int. Cl.
*A61K 31/5415* (2006.01)
*A61K 31/538* (2006.01)
(52) U.S. Cl. ...................................... 514/225.2; 544/42
(58) Field of Classification Search ................ 514/225.2
See application file for complete search history.

(56) References Cited

FOREIGN PATENT DOCUMENTS
WO WO-93/03029 A1 2/1993
WO WO-01/13918 A1 3/2001

OTHER PUBLICATIONS

International Search Report, PCT/EP2007/064553, issued Apr. 22, 2008.
Herbison et al., "Effectiveness of Anticholinergic Drugs Compared With Placebo in the Treatment of Overactive Bladder: Systematic Review", BMJ, vol. 326, Apr. 19, 2003, pp. 841-844.
Longhurst et al., "Characterization of the Functional Muscarinic Receptors in the Rat Urinary Bladder", B. Journal of Pharmacology, vol. 116, 1995, pp. 2279-2285.
Choppin et al., "Pharmacological Charaterization of Muscarinic Receptors in Rabbit Isolated Iris Sphincter Muscle and Urinary Bladder Smooth Muscle", Br. Journal of Pharmacology, vol. 124, 1998, pp. 863-868.
Chess-Williams et al., "The Minor Population of $M_3$-Receptors Mediate Contraction of Human Detrusor Muscle in Vitro", J. of Autonomic Pharmacology, vol. 21, 2001, pp. 243-248.
Matsui et al., "Multiple Functional Defects in Peripheral Autonomic Organs in Mice Lacking Muscarinic Acetylcholine Receptor Gene for the $M_3$ Subtype", PNAS, vol. 97, No. 17, Aug. 15, 2000, pp. 9579-9584.
Gillberg et al., "Comparison of the In Vitro and In Vivo Profiles of Tolterodine with Those of Subtype-Selective Muscarinic Receptor Antagonists", Eur. J. of Pharmacology, vol. 349, 1998, pp. 285-292.
Krichevsky et al., "Function of $M_3$ Muscarinic Receptors in the Rat Urinary Bladder Following Partial Outlet Obstruction", J. of Urology, vol. 161, May 1999, pp. 1644-1650.
Maruyama et al., "Human Muscarinic Receptor Binding Characteristics of Antimuscarinic Agents to Treat Overactive Bladder", J. of Urology, vol. 175, Jan. 2006, pp. 365-369.
Schroder et al., "Absorption of Oxybutynin from Vaginal Inserts Drug Blood Levels and the Response of the Rabbit Bladder", Urology, vol. 56, No. 6, Dec. 20, 2000, pp. 1063-1067.
Dorje et al., "Antagonist Binding Profiles of Five Cloned Human Muscarinic Receptor Subtypes[1]", J. Pharmacology and Exp. Therapeutics, vol. 256, No. 2, 1991, pp. 727-733.
Peralta, et al., "Distinct Primary Structures, Ligand-Binding Properties and Tissue-Specific Expression of Four Human Muscarinic Acetylcholine Receptors", EMBO Journal, vol. 6, No. 13, 1987, pp. 3923-3929.
Stanton et al., "Antagonism of the Five Cloned Human Muscarinic Cholinergic Receptors Expressed in CHO-K1 Cells by Antidepressants and Antihistaminics", Biochem, Pharmacology, vol. 45, No. 11, 1993, pp. 2352-2354.
Hedge, "Muscarinic Receptors in the Bladder: From Basic Research to Therapeutics", Br. Journal of Pharmacology, vol. 147, 2006, pp. S80-S87.
Dockhorn et al., "A Double-Blind, Placebo-Controlled Study of the Safety and Efficacy of Ipratropium Bromide Nasal Spray Versus Placebo in Patients with the Common Cold", J. Allergy Clin. Immunol., vol. 90, No. 6 II, Dec. 1992, pp. 1076-1082.
Starkman et al., "Management of Overactive Bladder with Transdermal Oxybutynin", Reviews in Urology, vol. 8, No. 3, 2006, pp. 93-97.
Yongtae et al., "Antimuscarinic Agents Exhibit Local Inhibitory Effects on Muscarinic Receptors in Bladder-Afferent Pathways", Journal of Urology, vol. 65, 2004, pp. 238-242.

*Primary Examiner* — Kahsay T Habte
(74) *Attorney, Agent, or Firm* — Birch, Stewart, Kolasch & Birch, LLP

(57) ABSTRACT

This invention relates to the use of 10-[(3R)-1-azabicyclo[2.2.2]oct-3-ylmethyl]-10H-phenothiazine as well as its pharmaceutically acceptable salts for the preparation of a drug having the particularity of treating or preventing urinary incontinence, by local and/or oral route.

10 Claims, No Drawings

USE OF 10-[(3R)-1-AZABICYCLO[2.2.2]OCT-3-YLMETHYL]-10H-PHENOTHIAZINE FOR THE PREPARATION OF A DRUG HAVING A SELECTIVE INHIBITION OF MUSCARINIC $M_1$, $M_2$, AND $M_3$ RECEPTORS

This invention relates to the use of 10-[(3R)-1-azabicyclo[2.2.2]oct-3-ylmethyl]-10H-phenothiazine as well as its pharmaceutically acceptable salts for the preparation of a drug making it possible in particular to prevent or treat urinary incontinence, by local and/or oral administration. 10-[(3R)-1-azabicyclo[2.2.2]oct-3-ylmethyl]-10H-phenothiazine, with a synthesis described in the patent, is derived from a racemate: d,l-mequitazine. Originally, mequitazine was a drug, effective in the treatment of allergic conditions such as seasonal or permanent allergic rhinitis, allergies to drugs, and dermatological manifestations of allergic or viral origin (pruritis). Mequitazine is an anti-H1 antihistamine. It possesses an asymmetric carbon leading to two distinct spatial configurations: levorotatory and dextrorotatory (R configuration). Exhaustive analysis of the properties of the two enantiomers showed that the dextrorotatory enantiomer had a very high affinity for the muscarinic receptors $M_1/M_2/M_3$, exemplified below, whereas the other enantiomer showed a lower affinity for the muscarinic receptors. Acetylcholine is the principal neuromediator of the parasympathetic nervous system. The physiologic actions of acetylcholine are mediated by muscarinic or nicotinic receptors. Each of these receptors is heterogeneous: e.g., the muscarinic receptor family comprises, at present, 5 sub-types (M.sub.1, M.sub.2, M.sub.3, M.sub.4, and M.sub.5). Each receptor is coded for by a different gene and possesses a distinct physiological distribution and function. However, several muscarinic receptors can work together to induce a common physiological effect, as is the case in the regulation of incontinence.

The $M_3$ receptor is one of the contributors to the contraction of the muscle involved in the control of the vesical sphincter (detrusor muscle of bladder: totality of the smooth musculature of the vesical wall/bladder).

There are causes responsible for incontinence which can be eliminated when they are identified: infection of the urinary tract, lithiase (stones) and constipation, for example. It also happens that a continence problem might be linked to treatment with drug. Incontinence may, in the elderly, correspond to a change in the living environment, to maladjustment to the environment. In the menopausal woman, the decrease in estrogenic saturation is often involved in the appearance of the phenomenon of incontinence, hormone substitution treatments belonging to the therapeutic arsenal in this population of patients. Outside of these circumstances, the cause of the incontinence can be identified by specific examinations. Management of incontinence may make use of drugs, re-education or, in some cases, surgery. Excessive reactivity of the bladder may be treated by specific antispasmodic drugs. Weakness of the sphincters may be improved by sympathomimetic drugs or, in women, by estrogenic hormones. Sympatholytic drugs may be used to relax over-contracted sphincters.

There are several types of urinary incontinence that are temporary or continuous according to the etiological factors. Thus the following are generally distinguished:
  incontinence from urgent micturation (hyper-reduced reflex of the detrusor), the abnormal contractions of the bladder occur involuntarily and lead to a pressing desire to urinate.
  urinary incontinence from stress.

These involve passive incontinence by reduction of urethral resistance. The urine leakage occurs when an abdominal pressure is exerted at the time of coughing, sneezing, etc.).
  incontinence of the neurogenic bladders, linked to vesicosphincteric dysfunction,
  incontinence from trauma,
  incontinence from ectopic anastomosis of the urethra,
  enuresis (in children over four years of age).

Incontinence from urgency, urinary incontinence from stress and incontinence from ectopic anastomosis of the urethra are found only in women, whereas that from overflow is masculine.

Primary treatment of the "hyperactive bladder" is based on the use of anticholinergic or antimuscarinic drugs. Recent meta-analyses show that the clinical benefit versus placebo is incontestable even if the treatment is accompanied by adverse effects like tachycardia, constipation or buccal dryness, which can explain the low compliance of patients to the treatment (Herbison P. et coll., BMJ, 2003). This is explained by the fact of the lack of vesical selectivity by the antimuscarinics with respect to other organs. Even if $M_2$ muscarinic receptors are those that are quantitatively the most expressed in the bladder and the lower urinary tract, this is proportionally the small fraction, and $M_3$ muscarinic receptors show themselves to be of greater importance on the plane of functional regulation of the contractions of the detrusor. In functional studies based on ex vivo models, using living detrusor fragments, it has been shown that $M_3$ sub-type of muscarinic receptor was identified as the only receptor sub-type involved in the contraction of the muscle in the rat (Longhurst P. A. et coll., Br. J. Pharmacol., 1995), in the rabbit (Choppin A., et coll., Brit. J. Pharmacol., 1998) and in man (Chess-Williams R., et coll., J. Auton. Pharmacol., 2002). These data relating the importance in terms of $M_3$ receptor regulation have been confirmed in models of transgenic mice deficient in the $M_3$ receptor (Matsui M., et coll., PNAS, 2000). On the mechanistic plane and in the normal state, acetylcholine fixes to the $M_3$ receptor, which releases the second messengers IP3 (inositol triphosphate) and DAG (diacylglycerol) inducing the contraction of smooth muscle. Acetylcholine also induces contraction by inhibiting the release of adenosine monophosphate and by reversing the relaxation induced by noradrenaline via the β receptors.

One of the major adverse effects of the use of anticholinergics in inhibition of incontinence is the phenomenon of buccal dryness. Paradoxically, it is by means of this effect that candidate drugs potentially useful in incontinence are selected in pharmacology, as is set out below. In preclinical animal studies, oxybutynine and darifenacine, two inhibitors used against incontinence, reduce salivation and are more selective with respect to the $M_3$ receptor than with respect to the $M_2$. In contrast, tolterodine reduces salivation less and is more active on the contractions of the detrusor. Tolterodine is more specific for the $M_2$ receptor than for the $M_3$ receptor (Gillberg P. G., et coll., Eur. J. Pharmacol., 1998). However, even if it was supposed that selectivity with respect to the $M_2$ or $M_3$ receptors could make it possible to differentiate the effects of the inhibitors, in the clinic the results are less clear and it appears that simultaneous action on the $M_2$ and $M_3$ receptors would be an efficacious combination with respect to incontinence syndromes. Thus, darifenacine which shows an affinity 7 times higher for $M_3$ muscarinic receptors than for $M_2$ muscarinic receptors, does not confirm vesical selectivity or toward the salivary glands. In conclusion, the $M_3$ receptors regulate the contractions of the smooth muscle of the bladder, and the $M_2$ receptors play a part in the initiation of this contraction (Krichevski V. P., et coll., J. Urol., 1999).

For the reasons previously cited, it appears that the candidate inhibitor should possess a mixed binding action to both the $M_2$ receptor and the $M_3$ receptor to have a complete action on the induction of contraction and on its regulation. In addition, the $M_1$ muscarinic receptor, which had been discredited in this field, seems also to play a role on the detrusor (Maruyama S., et coll., J. Urol., 2006).

For the purpose of reducing adverse effects induced by antimuscarinic agents, various devices have been used. They are transdermal, or placed in situ in the woman, in the form of sustained-release vaginal rings (Schröder A., et coll., Urol., 2000). Transdermal oxybutynine in the form of transdermal devices has been tested out with success, in order to limit the side-effects due to systemic dissemination of the active substance (Stakmann J. S., et coll., Urol., 2006). Through this route, the limitation of the effects or buccal or ocular dryness, vision problems, constipation and migraines is observed less; on the other hand, cutaneous intolerances to the device appear. Nevertheless, the phenomenon of initial hepatic passage is cancelled out, which limits the secondary activity induced by the very potent hepatic metabolite of oxibutynine (N-deoxybutynine), with a plasma level after oral oxibutynine administration 6 to 9 times greater than that of oxybutynine. It is the conjugation of these two entities that triggers the effects of inhibition of incontinence, as well as the induction of the side-effects.

Thus the limitation of the plasma level of active metabolites of the antimuscarinic drugs may also rest, besides on administration route specificity, on a specific hepatic metabolism not producing active metabolites, capable of exacerbating the effect of the initially administered drug, as well as increasing the frequency and intensity of the side-effects.

In addition, the longer the half-life of the product, the lower the frequency of administration, in this way facilitating compliance with the treatment.

The subject matter of this invention is based on the specific and unexpected properties of 10-[(3R)-1-azabicyclo[2.2.2]oct-3-ylmethyl]-10H-phenothiazine (dextrorotatory enantiomer of mequitazine, codified here under the name V0162). The examples below show that:
- the affinity with respect to the human $M_1$, $M_2$, $M_3$ muscarinic receptors is very powerful and in the nanomolar range,
- the dextrorotatory enantiomer (V0162) has more affinity than the racemate and than the levorotatory enantiomer, with respect to the muscarinic receptors,
- muscarinic targeting is mixed with, in order of affinity: $M_1 > M_3 > M_2$, this inhibition being qualitatively and quantitatively judged optimal for inhibition of the phenomenon of incontinence,
- in vivo the dextrorotatory enantiomer is anticholinergic by intravenous administration whereas the levorotatory enantiomer does not demonstrate clear activity. It is the same for oral administration,
- in vivo mucosal application of V0162 in suspension is expressed by clear systemic passage leading to a circulating level compatible with pharmacological activity with respect to muscarinic receptor targets,
- in vivo in a sialorrhea model in the rat, V0162 induces a significant decrease in salivary secretions after oral administration,
- in vivo in the vesical hyperactivity model (urgent incontinence) induced by exposure to acetic acid, V0162 reduces intravesical pressure evaluated by cystomanometry.

The combination of all these properties, taken up by way of examples of this patent, shows in an unexpected way that V0162 (10-[(3R)-1-azabicyclo[2.2.2]oct-3-ylmethyl]-10H-phenothiazine) is an active compound in urinary incontinence and the problems associated with it.

EXAMPLE 1

Affinity of V0162 (10-[(3R)-1-azabicyclo[2.2.2]oct-3-ylmethyl]-10H-phenothiazine) with respect to human muscarinic receptors, in vitro.

The purpose of this study is to determine an affinity constant for the compound with respect to the three classes of human muscarinic receptors in vitro. The model chosen is the CHO cell stably transfected with cDNAs coding for each of the three human muscarinic receptors. To begin with, a determination is made of the affinity of the cells expressing each type of receptor for a ligand for which 100% fixation to the target muscarinic receptor has been established. The optimal ligand for recombinant receptor $M_1$ is tritiated pirenzepine at 2 nM (Dorje F., et coll, JPET, 1991), that for recombinant receptor $M_2$ is tritiated methoctramine at 2 nM, that for receptor $M_3$ is 4-DAMP at 0.2 nM (Peralta E. G., et coll., EMBO, 1987). The binding specificity of the receptors expressed by each cell type was verified in parallel by evaluating the non-fixation of atropine at 1 µM. Binding with respect to the receptors is defined as follows: the difference between overall binding and non-specific binding determined in the presence of excess cold ligand. The results are expressed as a percentage of the optimal binding obtained with the model ligand (100%). The $IC_{50}$s (concentration necessary for 50% inhibition of the binding of the optimal ligand with its corresponding target receptor) and the Hill coefficients ($n_H$) were determined by non-linear regression analysis of the competition curves. The inhibition constants ($K_i$) were calculated by means of the Cheng Prusoff equation ($K_i = IC_{50}/(1+L/K_D)$); where L is the radioligand concentration and $K_D$ the affinity of the radioligand for the receptor.

TABLE 1

| V0162 Receptor Binding in vitro | | | | |
| --- | --- | --- | --- | --- |
| Human Receptors | Compound Tested | $IC_{50}$ (nM) | $K_i$ (nM) | $n_H$ |
| M1(h) | (10-[(3S)-1-azabicyclo[2.2.2]oct-3-ylmethyl]-10H-phenothiazine | 5.9 | 5.1 | 1.1 |
| | (10-[(3R)-1-azabicyclo[2.2.2]oct-3-ylmethyl]-10H-phenothiazine | 1.6 | 1.4 | 1.0 |
| | (10-[(3R,3S)-1-azabicyclo[2.2.2}oct-3-ylmethyl]-10H-phenothiazine | 2.1 | 1.8 | 0.8 |
| M2 (h) | (10-[(3S)-1-azabicyclo[2.2.2]oct-3-ylmethyl]-10H-phenothiazine | 94 | 66 | 1.0 |
| | (10-[(3R)-1-azabicyclo[2.2.2]oct-3-ylmethyl]-10H-phenothiazine | 10 | 7 | 1.1 |
| | (10-[(3R,3S)-1-azabicyclo[2.2.2}oct-3-ylmethyl]-10H-phenothiazine | 20 | 14 | 0.9 |
| M3 (h) | (10-[(3S)-1-azabicyclo[2.2.2]oct-3-ylmethyl]-10H-phenothiazine | 17 | 12 | 1.0 |
| | (10-[(3R)-1-azabicyclo[2.2.2]oct-3-ylmethyl]-10H-phenothiazine | 5.5 | 3.9 | 1.1 |
| | (10-[(3R,3S)-1-azabicyclo[2.2.2}oct-3-ylmethyl]-10H-phenothiazine | 8 | 5.7 | 1.2 |

These results show that V0162 ((10-[(3R)-1-azabicyclo[2.2.2]oct-3-ylmethyl]-10H-phenothiazine is a compound which binds strongly to the muscarinic receptors. Its specificity ratio $M_2/M_3$ is between 1.5 and 2. Its affinity for $M_1$ is also in the nanomolar range.

Thus, in vitro this compound demonstrates a very high affinity with respect to the muscarinic receptors involved in the initiation, regulation and maintenance of detrusor contractions. The differences between the enantiomers and the racemate with respect to these three receptors vary between a factor of 3 and a factor of 10, in terms of $K_i$.

EXAMPLE 2

Anticholinergic activity ex vivo of V0162 (10-[(3R)-1-azabicyclo[2.2.2]oct-3-ylmethyl]-10H-phenothiazine).

The purpose of these experiments was to confirm the anticholinergic activity of V0162 on a living organ. In order to do so, explants taken from the guinea pig were kept alive. The morphology of the preparations was homogeneous from batch to batch. Each explant was placed in a survival chamber and immersed in a physiological solution of composition (mM): NaCl (118); KCl (4.7); $MgSO_4$ (1.2); $CaCl_2$ (2.5); $KH_2PO_4$ (1.2); $NaHCO_3$ (25); glucose (11), at a temperature of 37° C. and with a pH of 7.4. Before the test, the following agents were dispersed in the survival buffer in order to block non-specific responses to acetylcholine: propanol ($10^{-6}$ M) to block $\beta_2$-adrenergic responses; cimetidine ($10^{-5}$ M) to block type 2 histaminergic responses; methysergide ($10^{-6}$ M) to block serotoninergic responses and indomethacine ($3\times10^{-6}$ M) to prevent the appearance of muscle tonus due to a release of prostaglandins by the preparation itself. At the time of acquisition, the tissues were connected to transponders in order to continuously record the variations in tension. After 60 minutes of calibration of the preparations, the tissues were exposed to variable concentrations of V0162. The contractions induced by acetylcholine as dose responses were carried out in order to determine the response of the preparation to the stimulation in the absence of the putative inhibitor.

TABLE 2

V0162, Anticholinergic Effect ex vivo

| Compound Tested | Concentration (nM) | Curves | Max. Response (%) | $EC_{50}$ ($\times 10^{-6}$ M) |
|---|---|---|---|---|
| V0162 | 0 | Control | 100 | 7.6 ± 2 |
|  | 30 | Test | 98 ± 1 | 22.5 ± 2.4*# |
|  | 0 | Control | 100 | 5.4 ± 0.8 |
|  | 100 | Test | 98 ± 1 | 76.0 ± 3.6*# |
|  | 0 | Control | 100 | 7.4 ± 0.5 |
|  | 300 | Test | 98 ± 1 | 410 ± 76.7*# |

Expression of results in the form of averages ± sem with n = 6 per group;
*p < 0.05 intra and
p < 0.05 extra The anticholinergic evaluation system is validated by the dose-effects obtained with acetylcholine as physiological mediator of muscle contraction. These results analyzed by Student's "t" test for unpaired values show that V0162 opposes the contractile action of acetylcholine. In this ex vivo model, the data obtained in vitro were confirmed: V0162 behaves like an antagonistic competitor of acetylcholine. Its action begins at 30 nM.

EXAMPLE 3

Sialorrhea inhibition activity of V0162 (10-[(3R)-1-azabicyclo[2.2.2]oct-3-ylmethyl]-10H-phenothiazine), in vivo.

Anticholinergic activity having been demonstrated in vitro at the cell receptor level and then ex vivo at the level of the target tissue, the objective of these experiments was to determine whether, after oral administration, an inhibition of salivary secretion appeared. Blockage of the $M_3$ receptors, involved in detrusor contractions and salivary secretion, often causes the phenomenon of buccal dryness as a concomitant effect of incontinence treatment by oxybutynine or tolterodine. The investigations on the new incontinence inhibitory agents have for a long time been based on receptor selectivity. It was assumed that the specificity of an agent with respect to $M_3$ receptors rather than $M_2$ receptors would make it possible to limit inhibition to the areas of receptor expression and therefore to avoid inhibition of physiological targets not involved in incontinence, such as for example the cardiac system or the salivary glands. However, as we have seen previously, the selectivity of the agents for fighting incontinence do not depend exclusively on tissue selectivity of the expression of muscarinic receptor sub-type. Indeed, the distribution of these receptors is not really linked to a tissue difference (i.e.: $M_2$ receptors are also found in the detrusor). On the functional plane, activation of certain receptors controls the level of activation of other receptors of the same muscarinic family. Thus, elimination of the compounds capable of affecting salivary secretion, for the purpose of selecting compounds active exclusively on the detrusor (and therefore on incontinence), leads to nonsense. Consequently the latest developments are pushing toward evaluation of agents for fighting incontinence in tests on inhibition of salivary secretion. A major point is the capacity of the compound to diffuse toward a target tissue. Thus, compounds capable of inhibiting salivary secretion in the ex vivo or even in vivo models in the animal may turn out to be lacking in effects on clinical buccal dryness in man. It nonetheless remains that the activity of inhibition of salivary secretion constitutes a sure tool of choice for anticholinergic activity.

For the purpose of evaluating anticholinergic activity in the validated model of pilocarpine-induced sialorrhea in the rat, groups of animals were fasted and the next day the products were administered orally 90 minutes before intra-peritoneal injection of pilocarpine (0.5 mg.kg$^{-1}$). The compounds tested were administered in doses of 2.5, 5 and 10 mg.kg$^{-1}$. Beforehand, the V0162 (10-[(3R)-1-azabicyclo[2.2.2]oct-3-ylmethyl]-10H-Phenothiazine) was suspended in a vehicle: carboxymethylcellulose at 0.5%. Atropine as positive experimental control was administered at the dose of 1 mg.kg$^{-1}$. The animals were anaesthetized and then the salivary secretion was collected for 60 minutes, every ten minutes. The samples were then dried and weighed.

TABLE 3

Inhibition of salivary secretion in the rat after p.o. administration, anticholinergic effect in vivo

| Treatment | n | Dose (mg · kg$^{-1}$) | Secretion (mg) | Inhibition (%) |
|---|---|---|---|---|
| Vehicle | 10 | — | 1045.8 | — |
| V0162 | 10 | 2.5 | 735.6 | 29 |
| V0162 | 10 | 5 | 338.9 | 67* |
| V0162 | 10 | 10 | 45.1 | 95* |
| Atropine | 10 | 1 | 17.9 | 98* |

Expression of the results in the form of averages with n = 10 per group;
*p < 0.05

The sialorrhea evaluation system is validated by the action of atropine in the model. The results show that the compound cited as example significantly reduces salivary secretion in the animal, after oral administration. The effects obtained are dose-dependent: The potency of compound V0162 (10-[(3R)-1-azabicyclo[2.2.2]oct-3-ylmethyl]-10H-phenothiazine) is similar to that obtained with the atropine used here as standard method. Thus, compound V0162 as well as its pharmaceutically acceptable salts turn out to be useful for the manufacture of drugs, in particular in a form adapted to nasal administration, for the treatment of rhinorrhea.

Subsequently, the anticholinergic activity of the two enantiomers was compared at a single dose, after oral administration according to the same experimental schema as that previously described.

TABLE 4

Inhibition of salivary secretion in the rat after p.o. administration of the racemic mixture and of the enantiomers, anticholinergic effect in vivo

| Treatment | n | Dose (mg · kg$^{-1}$) | Inhibition (%) |
|---|---|---|---|
| Vehicle | 7 | — | — |
| Levorotatory enantiomer (10-[(3S)-1-azabicyclo[2.2.2]oct-3-ylmethyl]-10H-phenothiazine | 7 | 5 | −4 |
| Dextrorotatory enantiomer (V0162) (10-[(3R)-1-azabicyclo[2.2.2]oct-3-ylmethyl]-10H-phenothiazine) | 7 | 5 | 77* |
| ²Racemic mixture (10-[(3R,3S)-1-azabicyclo[2.2.2]oct-3-ylmethyl]-10H-phenothiazine | 6 | 5 | 73* |

Expression of results in the form of averages with n = 10 per group;
*p < 0.05

In conclusion, these experiments confirm the results previously obtained in vitro and ex vivo, and demonstrate in an unexpected way that V0162 (10-[(3R)-1-azabicyclo[2.2.2]oct-3-ylmethyl]-10H-phenthiazine) is a potent anticholinergic per os. Moreover, it belongs to the class of potential inhibitors of incontinence because, like oxibutyrine, darifenacine or tolterodine, it reduces salivary secretion in the animal, after administration of non-toxic and well-tolerated pharmacological doses.

In addition, contrary to what was expected, inhibition of the cholinergic pathway is only effective after treatment of the animals with the dextrorotatory enantiomer. The levorotatory enantiomer demonstrates an anticholinergic activity in vitro, but these results are not the same after administration per os.

Thus, these results show that only V0162 exerts an anticholinergic activity in vivo.

EXAMPLE 4

Transmucosal passage of a suspension of V0162 (10-[(3R)-1-azabicyclo[2.2.2]oct-3-ylmethyl]-10H-phenothiazine), in vivo in the rabbit.

We have seen that the compound was capable of inducing anticholinergic activity after oral administration. Furthermore, it has been established that the selectivity of the action of the anticholinergics on the urinary system, for the purpose of inhibiting the contractions of the detrusor and therefore incontinence, does not rest on selectivity with respect to the sub-types of muscarinic receptors, because they are ubiquitously expressed. Thus, one of the means for arriving at selectivity is to reduce the systemic circulation of the antimuscarinics while increasing their concentration at their site of action: the lower urinary tract. Vaginal application of this compound could make it possible to limit side-effects while increasing efficacy. On the pharmacological plane the bladder may be separated into two: the body and the base. The muscarinic receptors are distributed predominantly in the body, and the contractile response to cholinergic stimulations is located at the same level. In the same way, the other mechanism involved in the maintenance of continence, direct activity on muscle relaxation, sees its control located at the same place. Moreover, recent work has shown the possibility of reducing the contractions of the bladder by local injection of anticholinergic agents. Thus, the anticholinergics could act not only as antagonists of acetylcholine in detrusor muscle contraction, but also by blocking the muscarinic receptors of the afferent paths of the bladder.

Consequently, in situ use of an antagonist compound would constitute an approach of choice for the treatment of incontinence in particular in the menopausal woman. The major restriction is the capacity of the antimuscarinic agent to cross the vaginal mucosa in order to target the muscarinic afferences in the neighbourhood of the bladder (Yongtae K., et coll., J. Urol., 2005).

For the purpose of analyzing the propensity of the compound of interest to cross a model mucous membrane, V0162 was administered by spraying on the nasal mucosa in the rabbit, and then blood samples were taken for the purpose of measuring a potential circulating level of V0162. 48 rabbits were treated nasally daily for 28 days with a suspension titrated at 0.4% mass/volume. The 3 groups of animals were distributed in the following way: saline solution, vehicle, V0162. Each group was made up of males and females equally. Nasal administration of the suspension was carried out twice per day for 28 days. Plasma samples were taken on D1, D2, D7, D28, D35. The samples were analyzed by an LC/MS/MS method validated by assay of V0162.

TABLE 5

Circulating levels of V0162 after repeated nasal administrations

| Date and hour of sample | Level of V0162 (ng · mL$^{-1}$) |
|---|---|
| Day 1/before administration | BLQ |
| Day 1/4 hours after administration | 0.88 |
| Day 2/before administration | 0.22 |
| Day 7/before administration | 0.41 |
| Day 28/4 hours after administration | 1.35 |
| Day 28/24 hours after administration | 0.23 |
| Day 35/before administration | BLQ |

Expression of results in the form of averages with n = 10 per group;
BLQ: below limit of quantification The results show that nasal administration of a suspension of V0162 induces a circulating level in the neighbourhood of 4 nM, compatible with pharmacological action. Indeed, we have previously seen that the IC50 of V0162 was 5 nM for muscarinic receptor $M_3$ and 1 nM for muscarinic receptor $M_1$.

It may therefore be concluded that mucosal administration of V0162 is expressed by an effective passage compatible with the circulating levels required for its anticholinergic activity. This administration does not induce deleterious effects on the nasal mucosa. The circulating levels obtained do not lead to toxic effects in this model, on neither the histological plane nor on that of the vital functions: respiratory rhythm, heart rate, behaviour.

Thus it is possible to administer the compound of interest by simple application to the mucosa for the purpose of locally delivering the anticholinergic agent.

EXAMPLE 5

Incontinence inhibitory activity of a suspension of V0162 (10-[(3R)-1-azabicyclo[2.2.2]oct-3-ylmethyl]-10H-phenothiazine), in vivo.

The objective of this study was to measure intravesical pressure and salivation, in the animal, for the purpose of testing the uroselectivity of the anti-muscarinics, when they are administered orally and vaginally. In order to evaluate intravesical pressure, the bladders of the animals were catheterized in order to make possible recording (cystomanometry: continuous recording of the vesical pressure). The products to be tested were administered either per os at a dose of 5 mg.Kg$^{-1}$ or by local application of a suspension of V0162 at 0.4% in a vehicle with a base of cyclodextrin and arginine. The jugular vein was also cannulated in order to administer a muscarinic agonist: bethanechol (200 µg/kg, iv). At each administration of bethanechol, the variation of vesical pressure (ΔPV, mmHg) and the quantity of saliva (mg) were evaluated and quantified. The positive control was made up of a group of animals treated with oxybutyrine (Ditropan®; 10, 100 and 1000 µg/kg, iv).

The results (expressed only in the text) show that compared to oxybutyrine, V0162 orally or by local application significantly reduces the increase in intravesical pressure induced by the agonist of reference: bethanecol.

The preceding experiments show that compound V0162 is capable of inducing anticholinergic activity after oral administration. Moreover, the compound is capable of crossing the mucosa. Compound V0162 possesses the characteristics of a potent anticholinergic: nM in vitro and mg.kg$^{-1}$ per as in vivo. It is active by the oral route and can also be administered locally to the mucosa in the form of a gelled preparation for the purpose of targeting the area where the muscarinic receptors directly controlling or regulating continence are represented.

The invention claimed is:

1. A method of treating urinary incontinence of a living animal body, which disorder, affliction or pathology is responsive to selective inhibition of $M_1$, $M_2$, and $M_3$ muscarinic receptors, which method comprises the step of administering to said living animal body in need thereof a therapeutically effective amount of a 10-[(3R)-1-azabicyclo[2.2.2]oct-3-ylmethyl]-10H-phenothiazine, or a pharmaceutically acceptable salt thereof.

2. The method of treatment as claimed in claim 1, wherein the 10-[(3R)-1-azabicyclo[2.2.2]oct-3-ylmethyl]-10H-phenothiazine is in the form of a drug comprising a mixture selected from mixtures comprising at least 95-100% of 10-[(3R)-1-azabicyclo[2.2.2]oct-3-ylmethyl]-10H-phenothiazine, 96-100% of 10-[(3R)-1-azabicyclo [2.2.2]oct-3-ylmethyl]-10H-phenothiazine, 97-100% of 10-[(3R)-1-azabicyclo [2.2.2]oct-3-ylmethyl]-10H-phenothiazine, 98-100% of 10-[(3R)-1-azabicyclo [2.2.2]oct-3-ylmethyl]-10H-phenothiazine, 99-100% of 10-[(3R)-1-azabicyclo [2.2.2]oct-3-ylmethyl]-10H-phenothiazine, and pure 10-[(3R)-1-azabicyclo[2.2.2]oct-3-ylmethyl]-10H-phenothiazine.

3. The method of treatment as claimed in claim 1, wherein the urinary incontinence is selected from the group consisting of: incontinence by urgent micturation by hyper-reduced reflux of the destrusor; abnormal contractions of the bladder occurring involuntarily and leading to a pressing desire to urinate; urinary incontinence from stress; incontinence of the neurogenic bladders, linked to vesico-sphincteric dysfunction; incontinence from trauma; incontinence from ectopic anastomosis of the urethra; and enuresis in children over four years of age.

4. The method of treatment as claimed in claim 1, wherein the drug is presented in a form adapted to oral administration.

5. The method of treatment as claimed in claim 1, wherein the drug is presented in an oral dosage form at a dose between 1 µg.kg$^{-1}$ and 10 mg.kg$^{-1}$.

6. The method of treatment as claimed in claim 1, wherein the drug is presented in a local intravaginal dosage form as a gel of active substance concentration between 0.01% and 10%.

7. The method of treatment as claimed in claim 1, wherein this drug is presented in a local intravaginal dosage form as an ovule, in a suppository comprising between 10 mg and 500 mg of active substance equivalent.

8. The method of treatment as claimed in claim 1, wherein the drug is in the form of a vaginal ring sustained release device, at a dose making possible the release into the perimucosal circulation of 0.2 ng to 100 ng of 10-[(3R)-1-azabicyclo[2.2.2]oct-3-ylmethyl]-10H-phenothiazine per mL of plasma.

9. The method of treatment as claimed in claim 1, wherein the drug is presented in an oral dosage form at a dose between 0.01 mg.kg$^{-1}$ and 1 mg.kg$^{-1}$.

10. The method of treatment as claimed in claim 1, wherein the drug is in the form of a vaginal ring sustained release device, at a dose making possible the release into the perimucosal circulation of 2 ng to 50 ng of 10-[(3R)-1-azabicyclo [2.2.2]oct-3-ylmethyl]-10H-phenothiazine per mL of plasma.

* * * * *